US 12,396,636 B2

(12) United States Patent
Hernandez Leal

(10) Patent No.: US 12,396,636 B2
(45) Date of Patent: Aug. 26, 2025

(54) ERGONOMIC REFRACTION STATION AND METHOD FOR USING SAME

(71) Applicant: Hernando Hernandez Leal, Bogota (CO)

(72) Inventor: Hernando Hernandez Leal, Bogota (CO)

( * ) Notice: Subject to any disclaimer, the term of this patent is extended or adjusted under 35 U.S.C. 154(b) by 0 days.

(21) Appl. No.: 18/081,465

(22) Filed: Dec. 14, 2022

(65) Prior Publication Data

US 2023/0233073 A1     Jul. 27, 2023

Related U.S. Application Data

(63) Continuation of application No. 16/474,518, filed as application No. PCT/CO2017/000011 on Dec. 18, 2017, now abandoned.

(30) Foreign Application Priority Data

Dec. 28, 2016    (CO) ............................. 20160006054

(51) Int. Cl.
    *A61B 3/02*          (2006.01)
    *A61B 3/00*          (2006.01)
               (Continued)

(52) U.S. Cl.
    CPC .......... *A61B 3/0285* (2013.01); *A61B 3/0025* (2013.01); *A61B 3/0041* (2013.01);
               (Continued)

(58) Field of Classification Search
    CPC ......... A61B 3/103; A61B 3/14; A61B 3/0285; A61B 3/113; A61B 3/024; A61B 3/032; A61B 3/04; A61B 3/18
               (Continued)

(56) References Cited

U.S. PATENT DOCUMENTS 2,835,161 A     5/1958    Williams
4,500,180 A     2/1985    Stevens
              (Continued)

FOREIGN PATENT DOCUMENTS

JP         2004073412 A     3/2004
WO    WO-2013096775 A1 *   6/2013           A61B 3/0285

OTHER PUBLICATIONS

International Search Report and Written Opinion for PCT application No. PCT/CO2017/000011, issued on Jan. 24, 2019, ( pages).

(Continued)

*Primary Examiner* — Dawayne Pinkney
(74) *Attorney, Agent, or Firm* — The Morales Law Firm; Joseph L. Morales, Esq.

(57) ABSTRACT

Ergonomic refraction station and procedure of use consists of a phoropter helmet, chair, work table, monitor and electronic circuit, which seeks to perform a refraction test in the conditions most similar to the usual work environment of the patient, for this it consists of a lightweight phoropter helmet, which adjusts to the size of the user, made of transparent material to allow contact with its surroundings and execute the usual movements of head, neck, eyes and working distance, parameters that are captured by optical, distance and inclination sensors, located on the phoropter helmet or on the flexible and adjustable table with "swan neck" arms.

11 Claims, 16 Drawing Sheets

(51) Int. Cl.
*A61B 3/024* (2006.01)
*A61B 3/028* (2006.01)
*A61B 3/10* (2006.01)
*A61B 5/00* (2006.01)
*A61B 5/107* (2006.01)
*A61B 90/50* (2016.01)

(52) U.S. Cl.
CPC .............. *A61B 5/1079* (2013.01); *A61B 5/706* (2013.01); *A61B 2090/502* (2016.02); *A61B 2503/20* (2013.01); *A61B 2560/0425* (2013.01)

(58) Field of Classification Search
USPC ............... 351/200, 206, 209, 210, 222, 223, 351/233–235, 245
See application file for complete search history.

(56) References Cited

U.S. PATENT DOCUMENTS

| | | |
|---|---|---|
| 7,670,003 B2 | 3/2010 | Kendrick |
| 8,419,184 B1 | 4/2013 | Butler |
| 2003/0151721 A1 | 8/2003 | Lai et al. |
| 2006/0114413 A1 | 6/2006 | Hosoi |
| 2016/0309999 A1 | 10/2016 | Rousseau et al. |
| 2016/0310000 A1 | 10/2016 | Meneghini |
| 2018/0263488 A1* | 9/2018 | Pamplona ............ A61B 3/0041 |
| 2021/0290053 A1* | 9/2021 | Tran ........................ A61B 3/10 |

OTHER PUBLICATIONS

Translated International Search Report for PCT No. PCT/CO2017/000011, pages.

* cited by examiner

ERGONOMIC REFRACTION STATION AND METHOD FOR USING SAME

CROSS-REFERENCE TO RELATED APPLICATIONS

This application is a continuation of U.S. patent application Ser. No. 16/474,518, filed on Jun. 27, 2019, which claims benefit to and priority from PCT application no. PCT/CO2017/000011, filed on Dec. 18, 2017, the contents of each are hereby expressly incorporated by reference in their entirety.

BACKGROUND

Currently, a refraction unit consisting of tree, chair that rises and falls with reclining backrest, focused lighting that is graduated with rheostat, one of the swinging arms holds a device called a phoropter, the arm extends forward and backward, rises, falls and moves horizontally and has a terminal spike that fits into the phoropter secured by a captive fastener, the phoropter is suspended by the arm thus transmitting a rigidity in the manipulation that limits its movements, this implies that it is manipulated by the examiner abruptly and with discomfort in front of the patient and is perceived as a rigid and heavy element by the examinee on his face, said device is used in the refraction of the eye during the visual test to determine the refractive error and the prescription with lenses, contains monofocal spherical positive and negative lenses (51) and others cylinder lenses, step button (38) for the cylinder lenses, other attachments are the JCC (Jackson Crosscilindro), step button for "R", "PH" and others (37), Rihsley prisms (39), with vision zone restricted to the small diameter eyepieces, same eyepieces are used so that the patient through them reads the far optotype and the near vision charts without considering their natural movement of head, neck and eyes since the support of the phoropter does not allow this type of movements, nor the determination of the pantoscopic angle, in addition, as the phoropter is made of non-transparent materials, it prevents the perception of the environment, depth and working distance for the patient of the near and intermediate vision, on the other hand near vision charts are not designed according to work environment. During the eye examination, the patient sits and stands behind the phoropter looking through circular eyepieces a screen of optotypes located in front, at the optical infinity (20 feet or 6 meters), long-sighted patients whose disorder is corrected with bifocal or progressive lenses, do not perform a real test of future bifocal or progressive lenses to be used since these are not incorporated into the current phoropter so they are not used during the visual acuity test with lenses, they are only incorporated with monofocal lenses and it is not possible with lenses of test cases (they are also mono focal), so that, currently, lenses for far vision and near vision are tested separately, far, middle and near vision are never tested with multifocal lenses, so there is no certainty of the degree of comfort that the patient shall have when using multifocal lenses. As it is known, when prescribing progressive or multifocal lenses, one should take into account the panoramic pantoscopic angle of the frame, convergence vision and near and middle working distance, for example, for the use of the computer or a vernier in a workshop, using the current phoropter, it is not possible to measure and graduate by means of the phoropter the negative pantoscopic angle, nor the panoramic inclination or angle, nor to test the reading in different working distances.

DESCRIPTION

Figure 1:
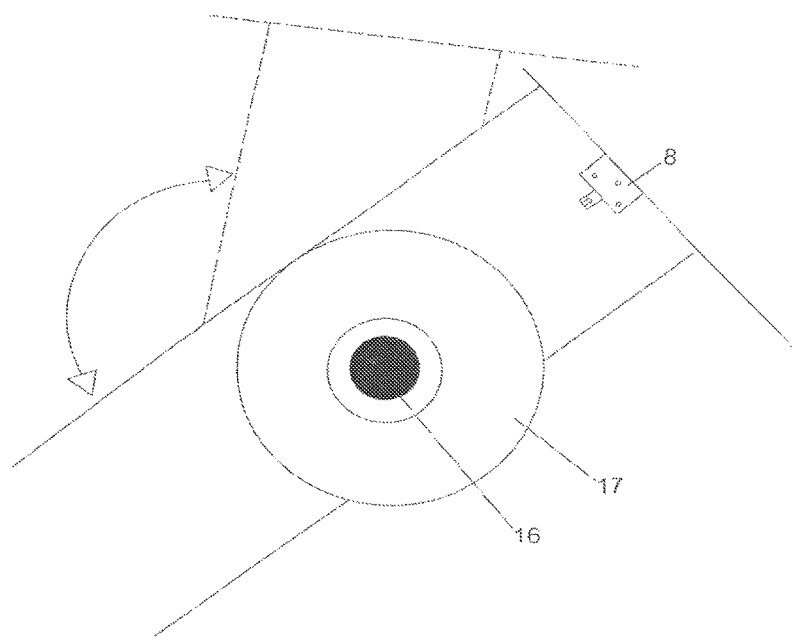
FIG. 1 is a side view of a flexible arm according to at least one instance of the present disclosure.
Figure 2:
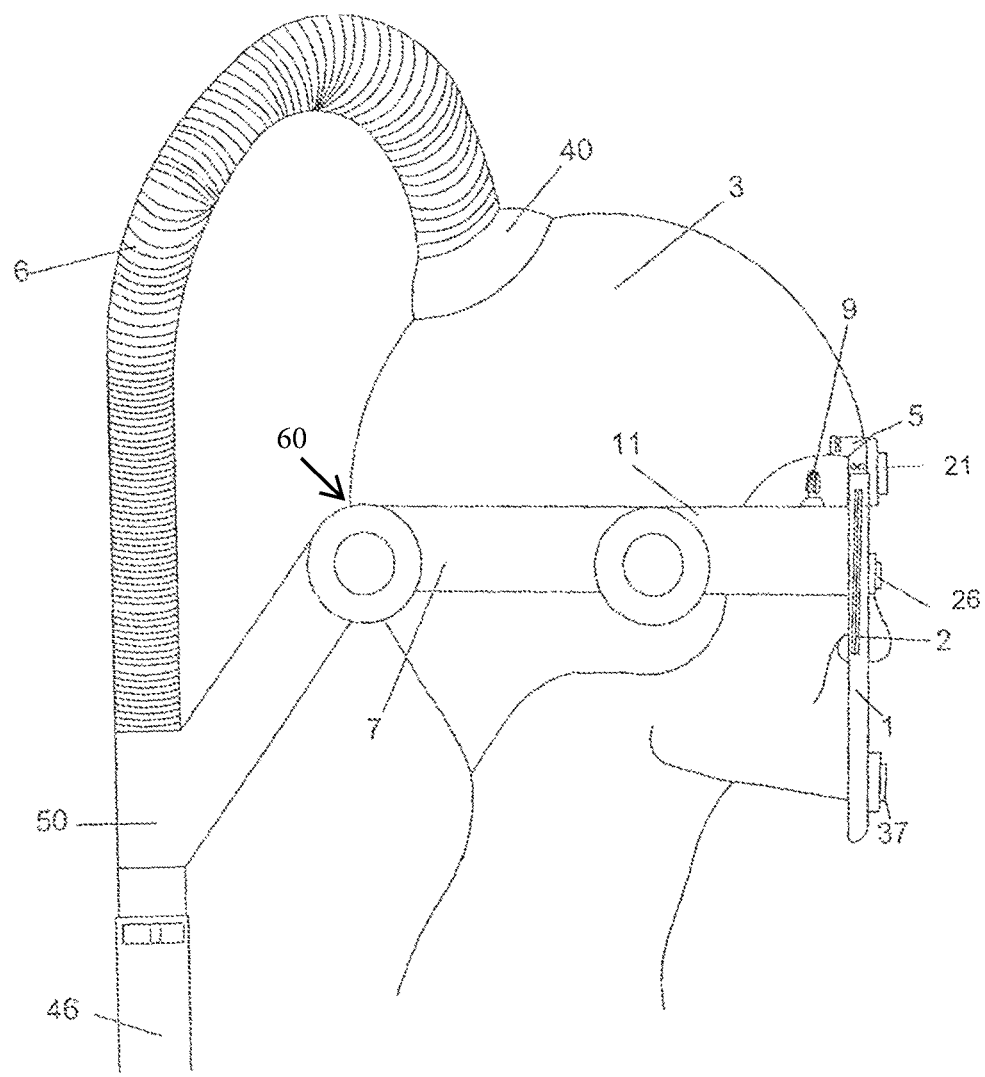
FIG. 2 is a side view of a phoropter helmet and support according to at least one instance of the present disclosure.
Figure 3:
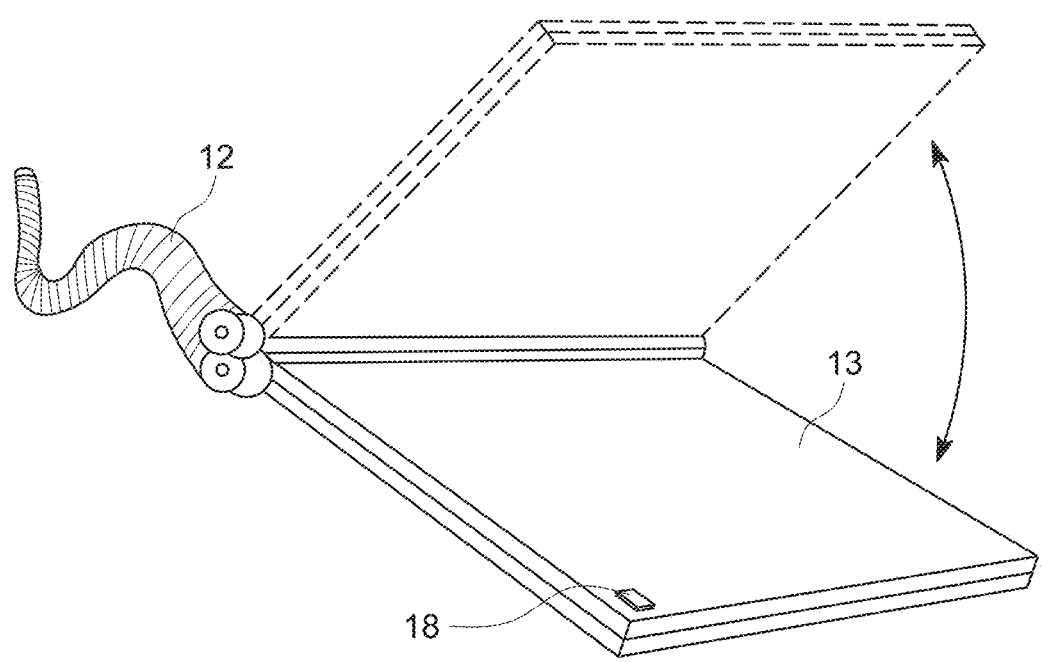
FIG. 3 is a diagrammatic view of a table according to at least one instance of the present disclosure.
Figure 4:
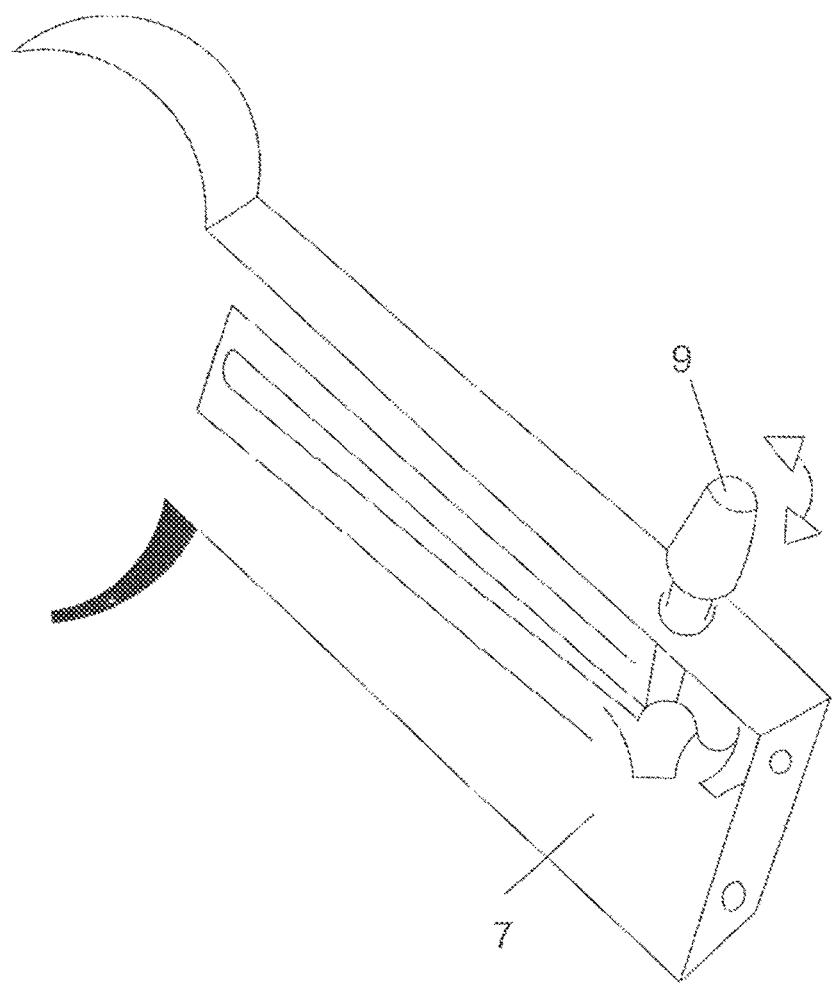
FIG. 4 is a diagrammatic view of a side arm according to at least one instance of the present disclosure.
Figure 5:
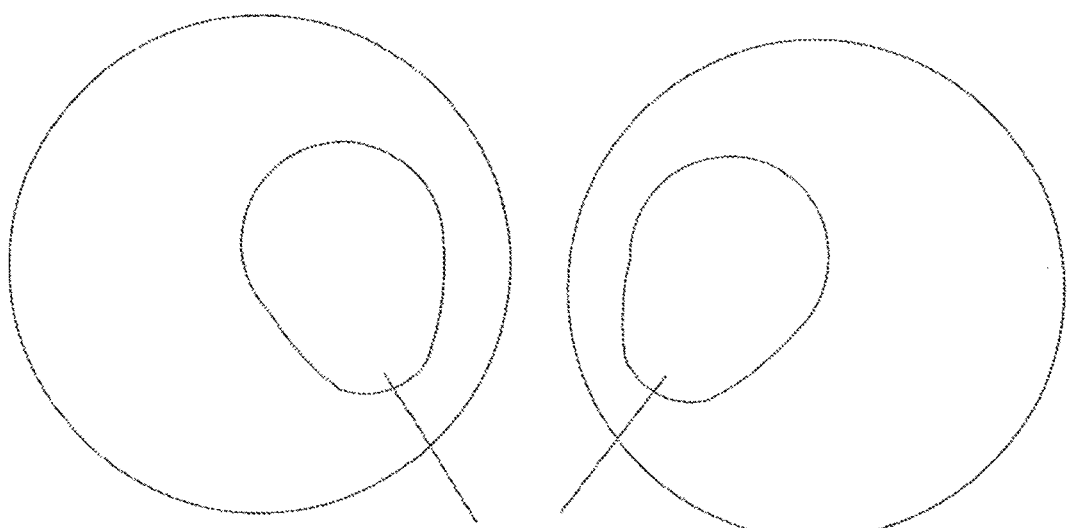
FIG. 5 is a diagrammatic view of eye pieces according to at least one instance of the present disclosure.
Figure 6:
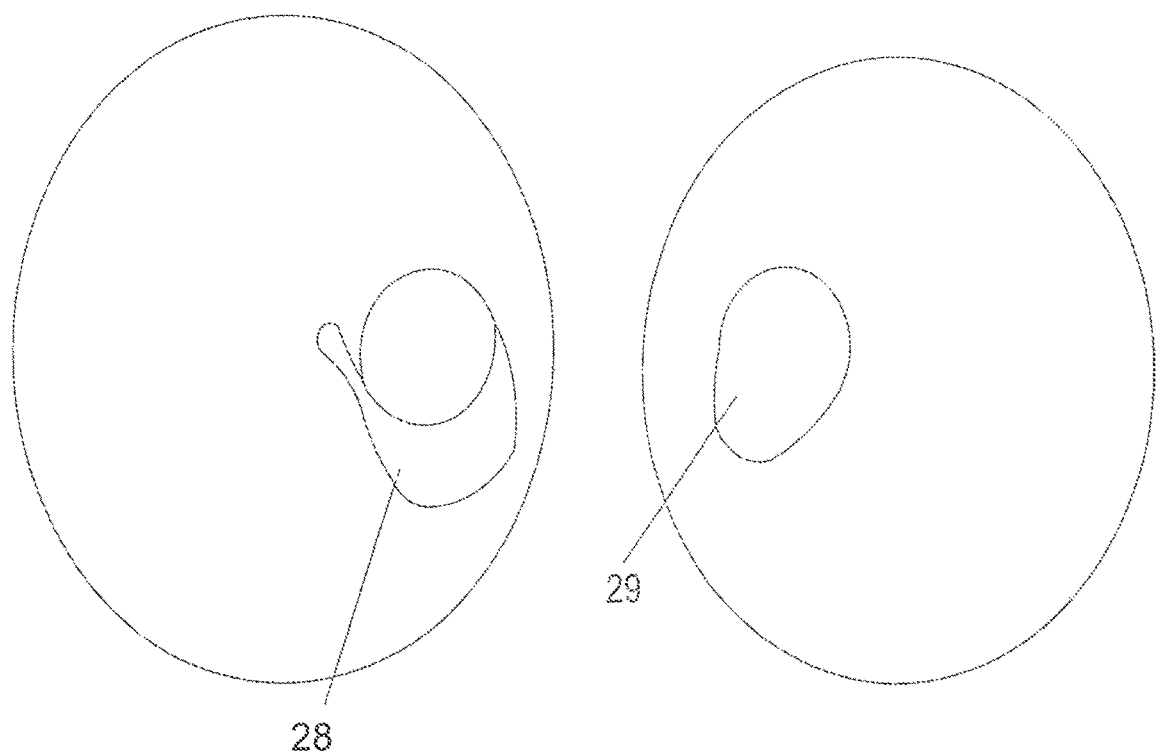
FIG. 6 is a diagrammatic view of eye piece covers according to at least one instance of the present disclosure.
Figure 7:
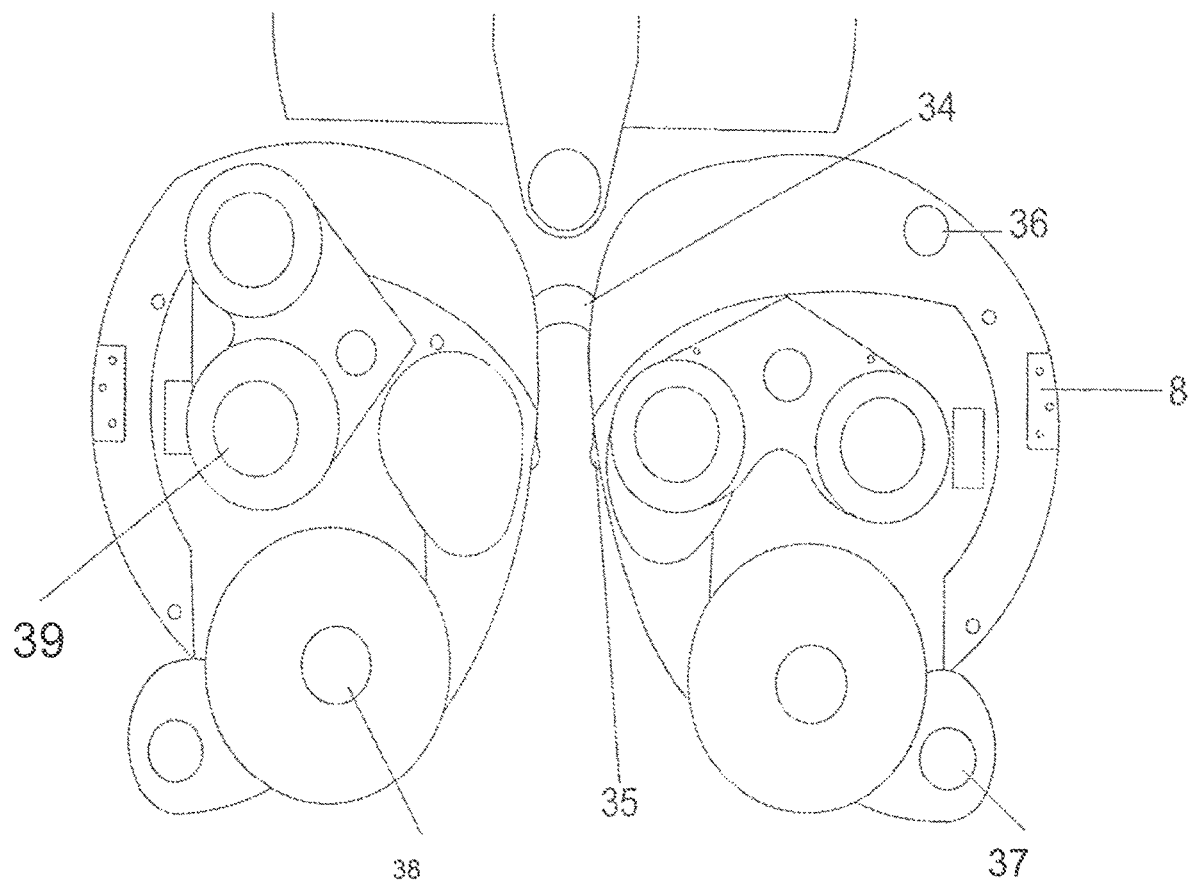
FIG. 7 is a front elevational view of a phoropter with a transparent casing according to at least one instance of the present disclosure.
Figure 8:
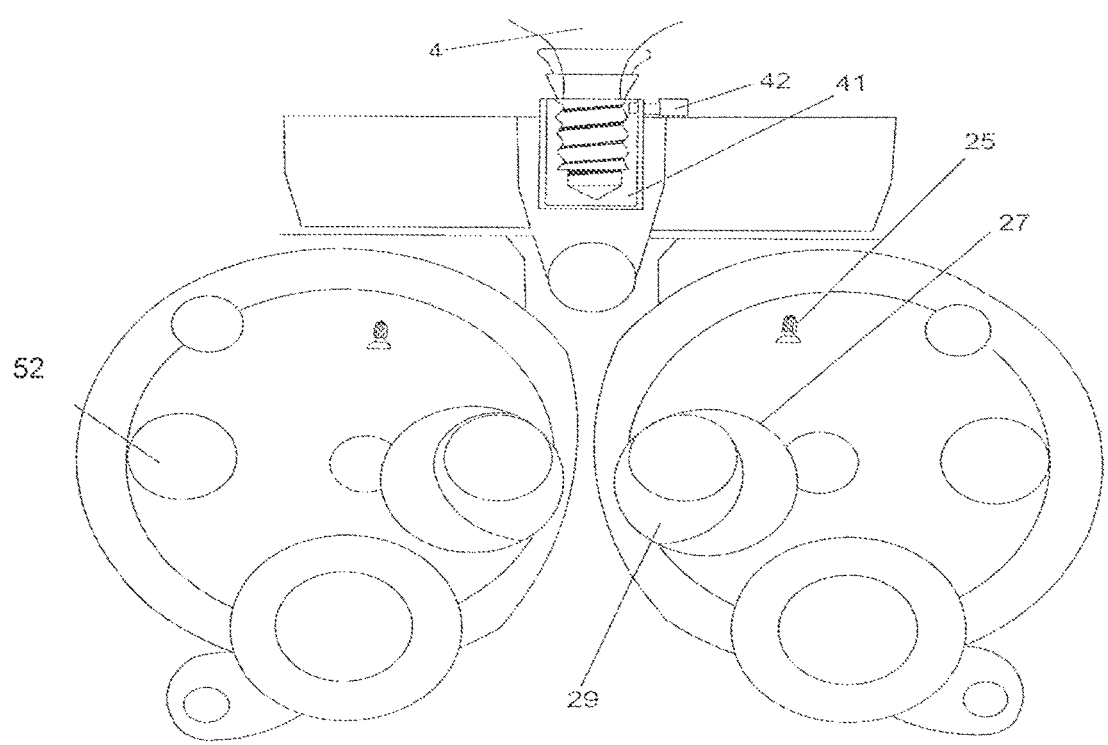
FIG. 8 is a diagrammatic view of a phoropter according to at least one instance of the present disclosure.
Figure 9:
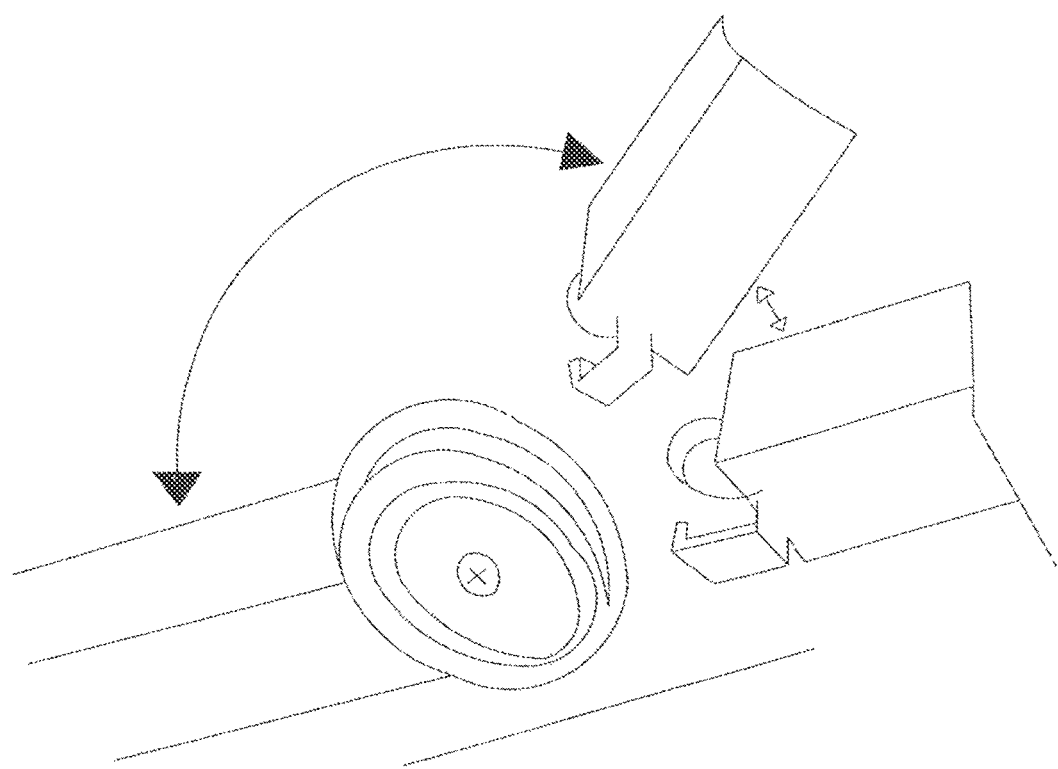
FIG. 9 is a diagrammatic view of a arm according to at least one instance of the present disclosure.
Figure 10:
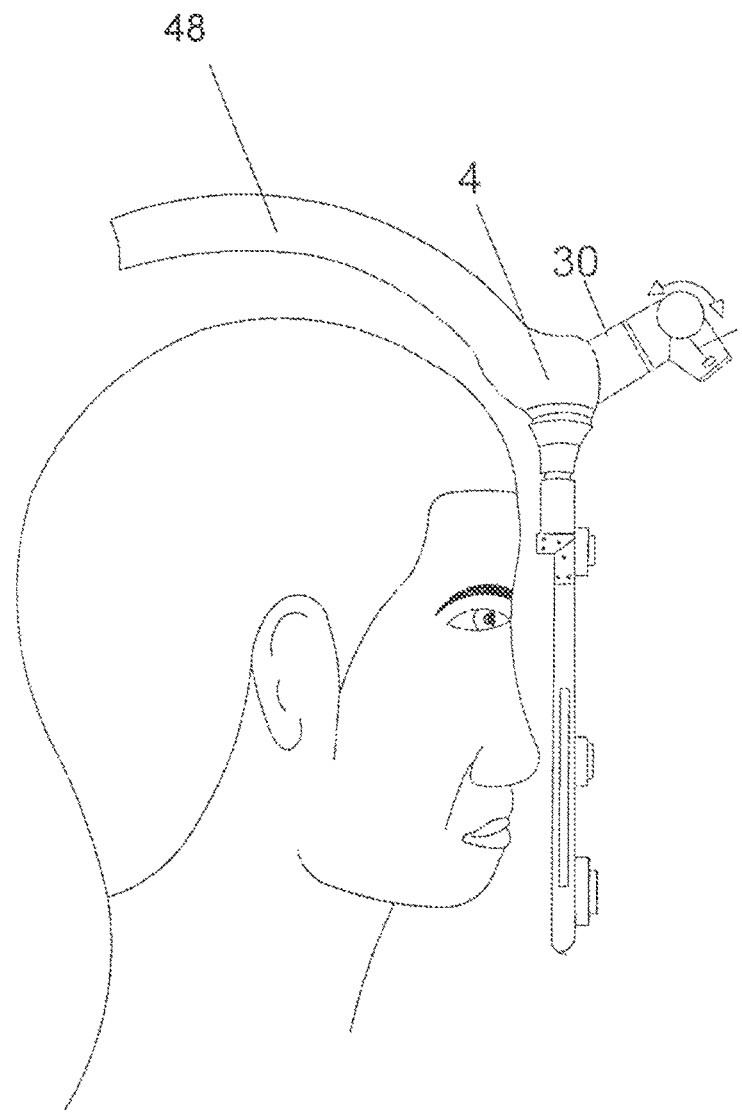
FIG. 10 is a diagrammatic view of a structural axis of a helmet and ball joint according to at least one instance of the present disclosure.
Figure 11:
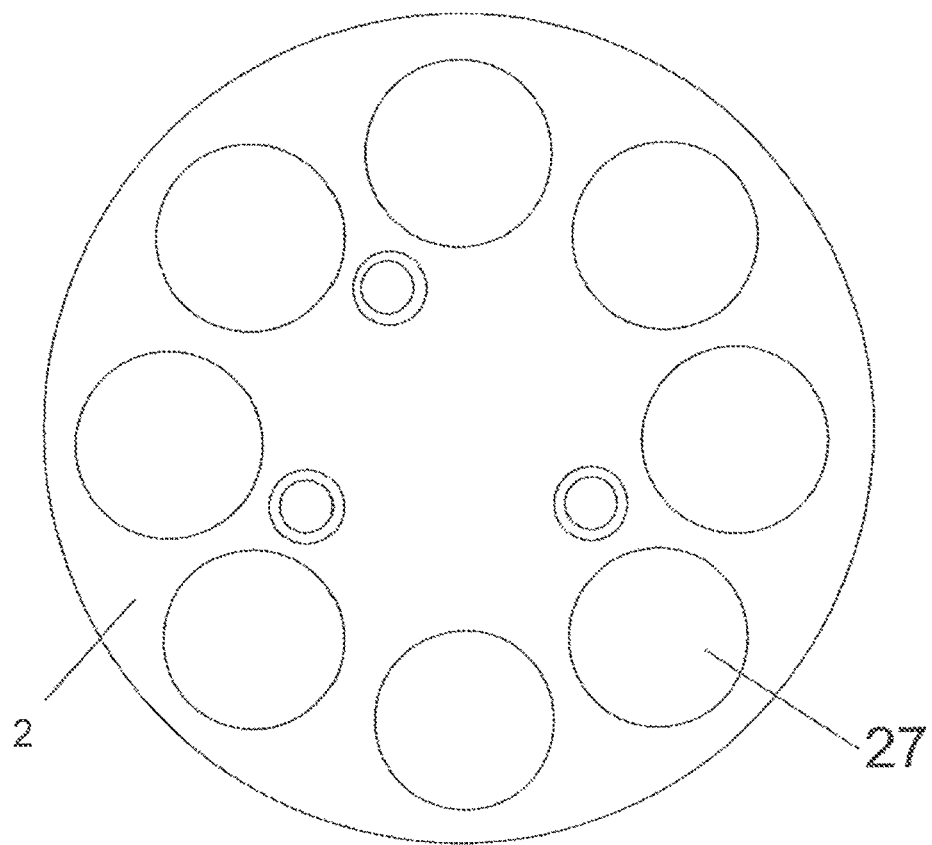
FIG. 11 is a diagrammatic view of a transparent crown for lenses according to at least one instance of the present disclosure.
Figure 12:
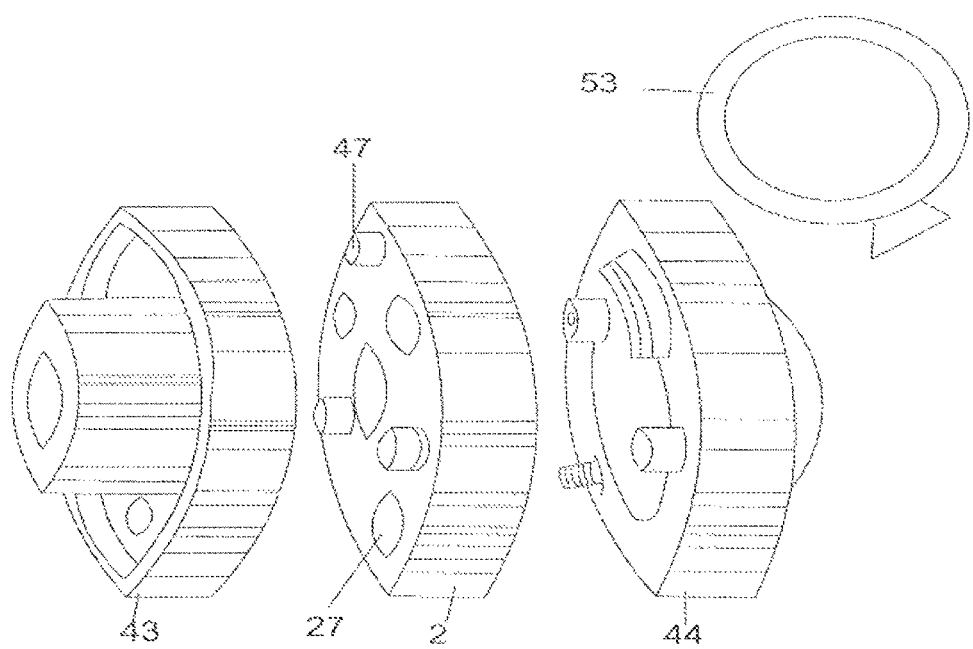
FIG. 12 is a diagrammatic view of a coupling, a crown, and a lenses holder according to at least one instance of the present disclosure.
Figure 13:
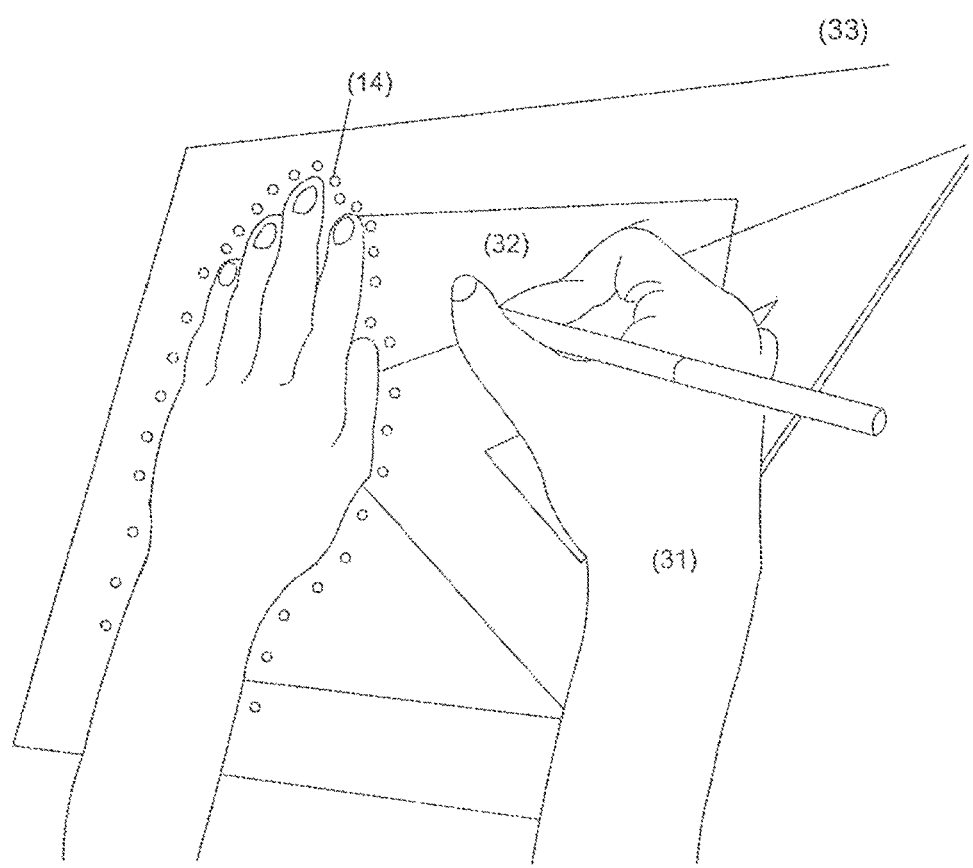
FIG. 13 is a diagrammatic view of an optical sensor and LED lights according to at least one instance of the present disclosure.
Figure 14:
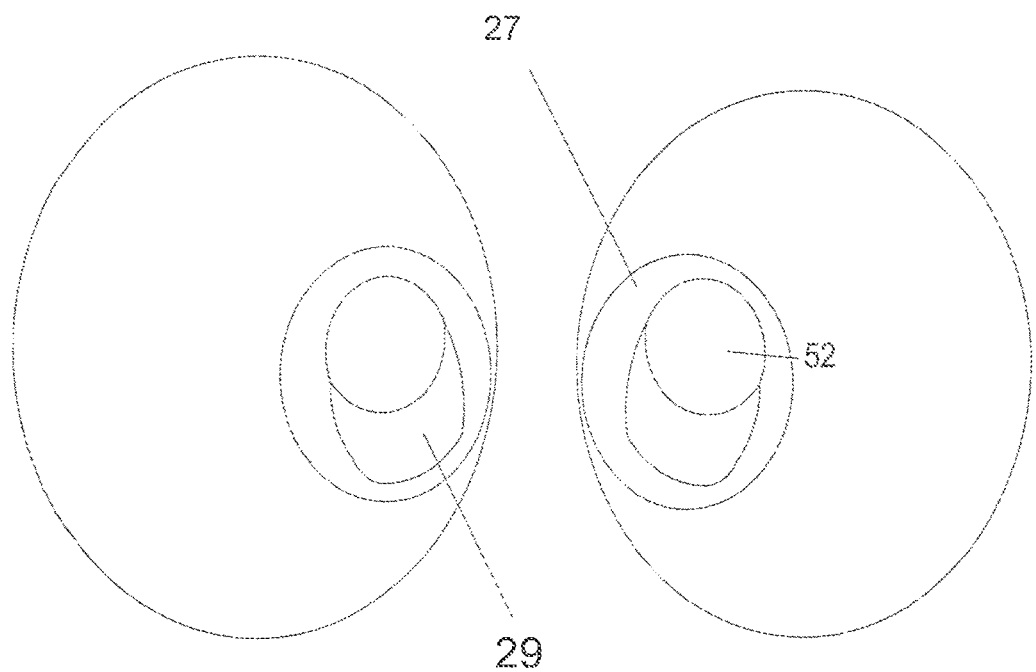
FIG. 14 is a diagrammatic view of mono focal, multifocal, and ocular lenses according to at least one instance of the present disclosure.
Figure 15:
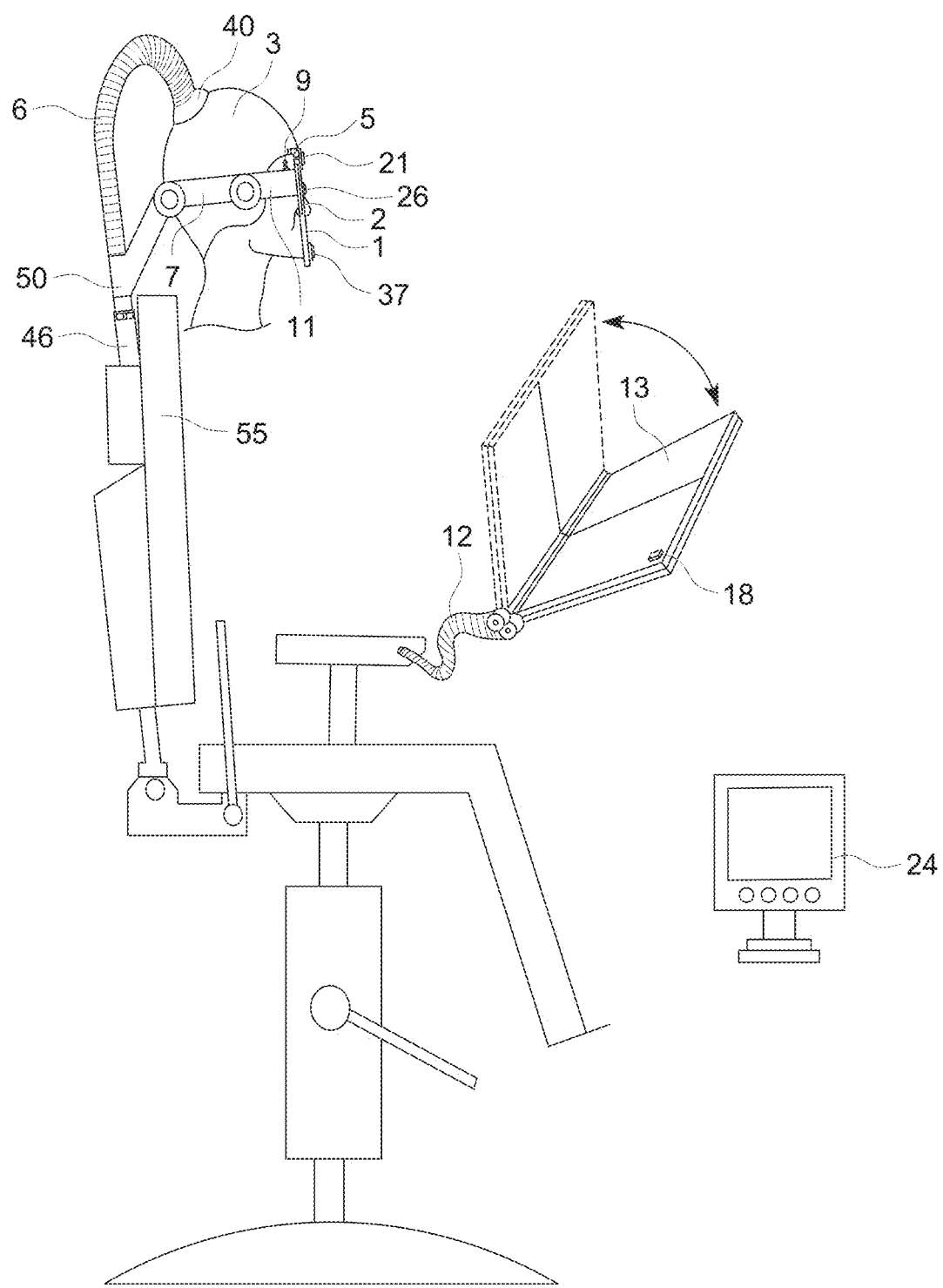
FIG. 15 is a diagrammatic view of a station according to at least one instance of the present disclosure.
Figure 16:
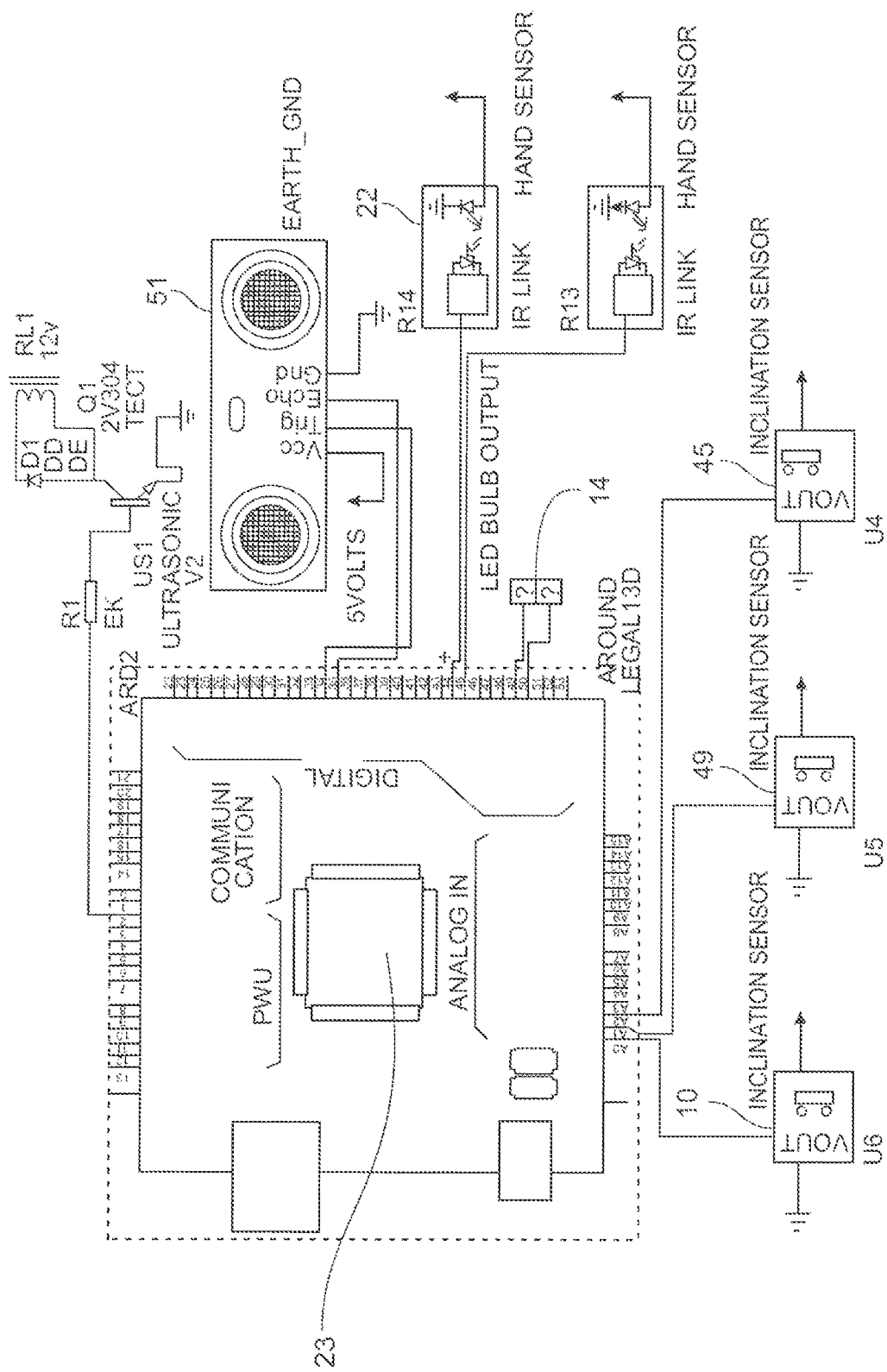
FIG. 16 is a diagrammatic view of a computing device according to at least one instance of the present disclosure.

Ergonomic refraction station and procedure of use, according to FIG. 15 in which the examinee graduates, adjusts and simulates each dimension according to its working environment, that is: inclination, lighting, distance, said station consists of a phoropter with casing (1) made of transparent, lightweight and resistant material, such as polycarbonate, crown for lenses made of transparent material (2), with mono focal lenses system and removable multifocal lenses, the proposed invention allows to see through the whole casing and improves the peripheral vision, the perception of the environment by the examinee, it makes it easier to estimate the working distance and depth, on its turn, the examiner perceives better through the transparent casing, the gestures, positions and movements of the patient, the non-metallic casing makes it lighter, it has rounded eyepieces wider than usual, in such a way that they allow far, medium and near vision field, arranged in V-shape, it has a helmet with a band that adjusts to the size of the head of the patient assembled with a ball joint to the phoropter, which facilitates its control with the movements of the patient's head and face, the patient being the one who directs the movements of the phoropter simulating the movements made by the head, neck and eyes in all directions when reading texts on far, middle and near distance vision charts, inclinations and angular measurements of the head and the phoropter helmet being recorded by inclination sensors incorporated into the station, in this way the phoropter is directed by the patient and not as before by the examiner, because thanks to its special characteristics: upper and front ball joints, light weight, weight reduction when removing multifocal lenses in non-long-sighted patients and supporting support that originates in the chair, it is the patient who directs the movement of the equipment simulating actual conditions of use of optical correction in the patient's habitual work station; the phoropter helmet does not require the tree of the traditional refraction unit nor the additional arm to support it, in addition, the ergonomic refraction station allows to determine the working reading distance even if the patient prefers standing, in the cases in which it is the patient's usual working position given the flexibility and lengthening of the swan arm and the chair sitting upright. Ergonomic, rotating chair that allows the examination in sitting and standing position, with adjustable height, backrest that runs back and forth, variable inclination seat. The phoropter helmet allows the visual acuity to be taken at far, medium and near distances registering the natural movement of the head, eyes and neck; software measures and shows the inclination of the reading table and head with respect to the horizontal and vertical, the working distance, the illumination of the surface required according to the job of the examinee, the helmet (3), with structural axis (48) and headband (60) adjustable to the size of the patient's head, supported by "swan neck" support (6), lower support (50) and on the upper part by a ball joint (40) that allows it to rotate in all directions, as the head of the patient may direct it with all comfort due to the ball joint system and the light weight of the phoropter, the frontal part thereof supported by two flexible side arms (7), thanks to the springs that reach each adjustable hinge (8) and the screws (9) forming the phoropter helmet assembly that facilitates the movement of the patient's head downwards when changing from looking to the front into focusing the near working distance; in its upper part the upper front ball joint (4), the side arms attach to the articulated joints or hinges (8) allowing the appropriate adjustment according to the size of the head and rest on the ears at a breaking angle of the terminal (11) also adjustable by the rotor (17). The phoropter helmet is moved by the patient, when introducing the head, lowers and raises the head with the help of the neck of the flexible support (6) as the patient would naturally do to work, lowers and inclines the head and the gaze forming and registering the pantoscopic angle, it also has speakers (16) for the output of incorporated sounds according to the selected work environment, at the same time being as an auditory reference when choosing the working distances at the moment of determining the addition for the formula of near or intermediate vision for working distances of the table, said table may have two or more complementary and assembled parts. It has concentric lenses (spherical and cylindrical) and incorporates multifocal lenses (27) having greater diameter than the previous ones that can be withdrawn or removed from the equipment to make it lighter in patients who do not require them as those who have not gotten presbyopia, only extracting the central pins (47) of the lens coupling system (26); eyepieces (29) arranged in the V-shape, with a distance from the far vision optical centers greater than the near vision distance for the determination of the addition that allow the test of the final prescription of glasses given the convergence in the near vision, movable eyepieces covers (28) that limit the use if it is required to test the vision only for far or all distances. A coupling (43) for the crown (2) of multifocal lenses and the lens holder (44) of the test case and progressive removable lenses, also has speakers to emit the sounds characteristic of the occupational environment, simulating the customized work environment, and projects an individualized test chart (32) according to the job on the rotary table (13), having variable height, which is incorporated in the refraction station, one of the chart models includes formulas for the case of a patient working as engineer, with characters of indicated size, contrast and lighting, which includes in its design figures of hands of different sizes (31) for different ages of the patient and is located in a designated place within the work environment that is projected on the table, the projected hands overlap or are aligned with those of the patient with the guide of led bulb lights (14) and with another figure of hands (15) projected on the table that the patient rotates until reaching the usual position of work, the hands projected on the table complement and overlap with parts of the hand that is drawn on the chart, both figures are guided by the LED lights when the patient places his/her hands and hand optical sensors (22), distributed on the table sends the information to the microprocessor that adjusts the size of the figures of hands to the real ones. Light LED sensors around and optical sensors in said figure, send the information to the microprocessor and it adjusts the projected size to the user size, likewise adjusts the size of the projected chart between the hands, distance sensor (20) measures the eye-hand distance and sends information to the microprocessor and it selects the size of the optotype and projects the line of visual acuity on the chart according to it, inclination sensor or electronic table compass (18) that sends the information to the microprocessor (23) about the angle of the table and relates it to the pantoscopic angle and it adjusts to the ergonomic reference values. Distance sensor (20) that sends information to microprocessor (23) and this one selects and shows on the monitor (24) the RI-lens or distance compensator. This improves the perception of distance and depth by the patient, including a software that sends the order to the adjustable projector (30) and it projects the optotypes that are images of a work environment on the table that also moves and tilts thanks to its support on two swan-neck arms (12) that come out of the chair of the station and that give it upwards, downwards, backwards and forwards and inclined movements that do not interfere with the armrests, with a tray or blade with support shaft (54) and rail (55) that slides forwards and backwards, adopts inclined positions, devices in front part (34) to place disposable and nose protector (35) including board holder to accommodate at that point of support on the patient's face, captive fastener (42), pantoscopic angle sensor (10) and levers (25) of positive and negative panoramic angle or button for adjusting monocular convergence, panoramic hinges (5) with pupil panoramic inclination sensor (49) for positive and negative or divergent angles. Side arms leave the lower support (50) which in turn engages the central axis of the support (46) in the lower part, projecting forward and upwards and from there they exit horizontally until the next hinge on the side front part of the phoropter; from the internal part of this hinge another arm adjustable with screw is detached that indicates the pantoscopic angle, adjustable to the size of the patient's head and with terminal at an angle of support on the ear or breaking angle. The software records all the working conditions for the clinical history of: surface illumination, inclination angle, letter size, working distance, pantoscopic angle, diopter, panoramic angle, back inclination, the chair can even vibrate as it happens when driving. Test charts for computerized projectors, with characters of size, contrast, characterized by figures of real-size hands (31) for the patient's age and located at a place (33) indicated within the work environment that is projected on the table, according to the job, it includes formulas for engineers, graphics and images related to the job, the hands are overlapped or aligned with the guide of lights, in the same way it adjusts the size of the projected chart between the hands, distance sensor sends information to the microprocessor and it selects the size of the optotype, the line of visual acuity on the chart and the inclination of characters of the chart according to the position of hands, head and eyes.

Procedure of the station: The information provided to the software in the anamnesis as age, sex, occupation, together with the options that the patient selects on his usual reading position at work, that is, body, head, eyes and hands position, they are analyzed by the software which then analyzes and decides on the ergonomic parameters for this subject, immediately the station comprising: the chair for sitting and standing position, rotating table and phoropter helmet adopt these positions, which is recorded by the inclination, panoramic, pantoscopic, table angle, head and articulated joints sensors, similarly, the hands of the examiner when resting on the table, activate the optical sensors, indicating to the microprocessor which is the actual size and position of the patient's hands, so that the figure of hands (15) projected onto the table tray (19), overlap or align with the patient ones with the guide of lights (14) on the table, which improves the perception of distance and depth by the patient, the software sends information of the angles of inclination of the head (inclination sensor located on the phoropter helmet) (45) and of the table, and of horizontal display, to the micro processor, it decides and orders to properly project the reading chart, this according to eye-hand and eye-hand visual-motor coordination, the microprocessor assembled to the arduino powered by 12 Volts, indicates the best working distance, letter size for 20/20, lighting quantity and direction, with the multifocal lens step button (36) the lens indicated for the age of the presbyopic patient is placed in front of the eyepiece.

The examinee selects on the monitor his/her usual work position, that is, the position of the body, head, eyes, hands, head-hand distance, lighting and environment sound. The software receives the information and indicates the ergonomic parameters for this subject and transfers them to the sensors of the ergonomic refraction station. The chair, adjustable rotating table and phoropter helmet adopt the indicated positions guided by the sensors of inclination: panoramic, pantoscopic angle, angle of table and head. The phoropter helmet is adjusted to the size of the patient's head. Distances are adjusted: chair height, table, table arms, "swan neck" support, side arms of phoropter. The examiner rests his hands on the table and activates the optical sensors (22) located on the table, which indicate to the micro processor which is the actual size and position of the patient's hands, until the figure of hands (15) projected on the table tray (19), overlap or align with the patient ones with the guide of lights (14) on the table. The hands projected on the table complement and overlap with parts of the hand that are drawn on the chart, both figures are guided by LED lights until the patient places his/her own hands, the sensor sends the information to the microprocessor (23) that adjust the size The microprocessor receives information about the inclination angle of the head (inclination sensor located on the phoropter helmet) (45), pantoscopic angle (10), panoramic angle (49) and angle of the table (18), so that the projector focuses on the reading chart. The microprocessor selects the letter size for the 20/20, of the chart, of the optotype, the amount of illumination, direction thereof, the line of visual acuity on the chart and the inclination of the characters of the chart according to the position of hands, head, eyes and working distance. The patient looks through transparent material of the casing and crowns and locates in the environment. The examiner adjusts angles: panoramic, pantoscopic, table and head, visualizes on monitor and counters the parameters of angles, distances, lighting, occupational chart. If the patient is presbyopic, the crown of multifocal lenses is attached in the front part, with the multifocal lens step button (36), the lens indicated for age is placed in front of the eyepiece and/or a multifocal lens (53) of the test case is placed. The eyepieces are cleared by moving the eye covers. Takes visual acuity in far, medium and near fields, the projector focuses on the occupational chart according to the job or profession and adjusts the size of the projected chart between the hands. A reading test is performed in the far, middle and near vision field using multifocal lenses. If necessary, the lens holder of the test case is attached.

The invention claimed is:

1. An ergonomic refraction station comprising:
    a rotating chair having a central axis of support, connected to a lower support;
    a swan neck support connected to the lower support of the central axis of support on one end and to a helmet-phoropter on a second end through a ball joint;
    the helmet-phoropter comprising a helmet and a lightweight headband adjustable to a size of a patient's head;
    the helmet further comprises a structural axis and an upper front ball joint, which connects to the phoropter through a base allowing the helmet to rotate;
    two side flexible arms coupled to a front middle part of the helmet-phoropter, the two side flexible arms are coupled to the phoropter by an articulated joint or hinge with a screw that can be adjusted and located on a back of a respective one of the two side flexible arms;
    each flexible arm further comprises a speaker;
    a lower support coupled to the swan neck support and having the two side flexible arms extending therefrom, the lower support being coupled, at an end opposite to the swan neck support, to a central axis of bottom support;
    two front covers and two back covers coupled to the helmet-phoropter made of transparent polycarbonate;
    a lens crown having a plurality of spherical lenses, a plurality of cylindrical lenses, and a plurality of removable multifocal lenses that have a diameter greater than a diameter of the spherical lenses and a diameter of the cylindrical lenses, wherein the plurality of removable multifocal lenses are concentric with the spherical lenses and cylindrical lenses;
    two adjustable side swan neck arms extending from the rotating chair and coupled to a work table;
    a plurality of LED bulbs forming a shape of a hand figure, whereby during examination the patient places his/her hand within the hand figure;
    a plurality of optical sensors operable to determine a position and size of the patient's hand;
    an electronic inclination sensor coupled to the work table and connected to an electronic circuit;
    a projector located in front of the helmet-phoropter;
    a microprocessor operable to:
        adjust a size of the hand figure on the work table;

receive data from the plurality of optical sensors concerning the position and size of a patient's hand and an electronic inclination sensor located within the helmet-phoropter for assessing a patient's head position;

select a vision chart comprising formulas, graphics, or images;

send a signal to the electronic circuit projector and emit sounds through the speaker;

select a font size, a size of the vision chart, an optotype, an amount of illumination, a line of visual acuity on the vision chart and an inclination of characters of the vision chart according to the position of a hand, head, eyes and working distance.

2. The ergonomic refraction station of claim 1, wherein the lens crown is made of polycarbonate.

3. The ergonomic refraction station of claim 1, wherein a terminal end of the two side flexible arms is curved.

4. The ergonomic refraction station of claim 1, wherein the helmet-phoropter includes a left lens crown and a right lens crown both made of polycarbonate.

5. The ergonomic refraction station of claim 1, wherein the microprocessor aligns the hand figure and the vision chart.

6. The ergonomic refraction station of claim 1, wherein the one or more sensors located within the helmet-phoropter including a distance sensor assembled on the ball joint and inclination sensors.

7. The ergonomic refraction station of claim 1, further comprising coupling system for the lens crown that includes one or more removable pins.

8. The ergonomic refraction station of claim 1, further comprising eyepieces arranged in V-shape.

9. The ergonomic refraction station of claim 8, further comprising eyepieces covers operable to cover the eyepieces.

10. The ergonomic refraction station of claim 1, further comprising:
an electronic pantoscopic angle sensor, a loudspeaker, a rotor, a lenses holder removable, a lever for positive and negative panoramic angle adjustment, a crown coupling having on external part a lenses holder, a step button coupled to the removable multifocal lenses.

11. A method for projecting a selected size chart on a table of the ergonomic refraction station, comprising:
providing an ergonomic refraction station comprising:
a rotating chair having a central axis of support, connected to a lower support;
a swan neck support connected to the lower support of the central axis of support on one end and to a helmet-phoropter on a second end through a ball joint;
the helmet-phoropter comprising a helmet and a lightweight headband adjustable to a size of a patient's head;
the helmet further comprises a structural axis and an upper front ball joint, which connects to the phoropter through a base;
two side flexible arms coupled to a front middle part of the helmet-phoropter, the two side flexible arms are coupled to the phoropter by an articulated joint or hinge with a screw that can be adjusted and located on a back of a respective one of the two side flexible arms;
each flexible arm further comprises a speaker;
a lower support coupled to the swan neck support and having the two side flexible arms extending therefrom, the lower support being coupled, at an end opposite to the swan neck support, to a central axis of bottom support;
two front covers and two back covers coupled to the helmet-phoropter made of transparent polycarbonate;
a lens crown having a plurality of spherical lenses, a plurality of cylindrical lenses, and a plurality of removable multifocal lenses that have a diameter greater than a diameter of the spherical lenses and a diameter of the cylindrical lenses, wherein the plurality of removable multifocal lenses are concentric with the spherical lenses and cylindrical lenses;
two adjustable side swan neck arms extending from the rotating chair and coupled to a work table, a plurality of LED bulbs forming a shape of a hand figure, whereby during examination the patient places his/her hand within the hand figure;
a plurality of optical sensors operable to determine a position and size of the patient's hand;
an electronic inclination sensor coupled to the work table and connected to an electronic circuit projector located in front of the helmet-phoropter for assessing a patient's head position;
a microprocessor operable to:
adjust a size of the hand figure on the work table;
receive data from the plurality of optical sensors concerning the position and size of a patient's hand and an electronic inclination sensor located within the helmet-phoropter for assessing a patient's head position;
select a vision chart comprising formulas, graphics, or images;
send a signal to the electronic circuit projector and emit sounds through the speaker;
select a font size, a size of the vision chart, an optotype, an amount of illumination, a line of visual acuity on the vision chart and an inclination of characters of the vision chart according to the position of a hand, head, eyes and working distance;
fitting the helmet-phoropter to a size of a head of the patient;
measuring an inclination of the helmet-phoropter and the table;
recording a pantoscopic angle;
observing through the multifocal lenses and through eyepieces;
measuring an eye-hand distance;
having a patient place their hands on the table and activating the optical sensors;
sending information to the microprocessor, which selects a distance compensating lens and a display on a monitor;
selects the size of the chart and the characters therein;
selects the inclination of characters;
adjust a pantoscopic angle;
sends a signal to the electronic circuit projector;
sends a signal to speakers;
projects the vision chart on the table;
passes a plurality of removable multifocal lenses with a step button.

* * * * *